United States Patent [19]
Valentine et al.

[11] Patent Number: 5,447,505
[45] Date of Patent: Sep. 5, 1995

[54] WOUND TREATMENT METHOD

[75] Inventors: Douglas R. Valentine, Oakdale; Ronald J. Cercone, East Lyme, both of Conn.; Mark K. Adams, Califon, N.J.

[73] Assignee: Merocel Corporation, Mystic, Conn.

[21] Appl. No.: 101,686

[22] Filed: Aug. 4, 1993

[51] Int. Cl.$^6$ .............................................. A61F 13/00
[52] U.S. Cl. ........................................ 604/304; 602/48
[58] Field of Search ............... 604/304, 307; 602/48, 602/50

[56] References Cited

U.S. PATENT DOCUMENTS

| | | | |
|---|---|---|---|
| 3,648,692 | 3/1972 | Wheeler | 128/156 |
| 3,983,209 | 9/1976 | Schmitt | 424/78 |
| 4,098,728 | 7/1978 | Rosenblatt | 521/141 |
| 4,292,972 | 10/1981 | Pawelchak et al. | 128/296 |
| 4,307,081 | 12/1981 | Klein et al. | 424/94 |
| 4,668,228 | 5/1987 | Bolton et al. | 604/307 |
| 4,759,354 | 7/1988 | Quarfoot et al. | 128/156 |
| 4,909,244 | 3/1990 | Quarfoot et al. | 128/156 |
| 5,115,801 | 5/1992 | Cartnell et al. | 602/48 |
| 5,154,706 | 10/1992 | Cartnell et al. | 604/304 |
| 5,160,328 | 11/1992 | Cartmell et al. | 604/307 |
| 5,204,110 | 4/1993 | Cartnell et al. | 602/48 |

OTHER PUBLICATIONS

*Synthetic Substitutes for Skin,* Chardack et al., Plastic In Reconstruction Surgery, vol. 39, No. 5, (Nov. 1962).

*Primary Examiner*—Jerome L. Kruter
*Attorney, Agent, or Firm*—Gipple & Hale; John S. Hale

[57] ABSTRACT

A method of treatment of Stage II, III and IV wounds in human beings comprising the steps of: inserting a surgical dressing constructed of a polyvinyl acetal having a pore diameter ranging from about 0.3 to about 1. mm into an open wound so that it conforms to the general configuration of the open wound; allowing the surgical dressing to remain in the wound to autolyze slough and necrotic tissue from the wound and absorb wound exudate from the wound; and removing the surgical dressing to selectively atraumatically debride the wound without damaging granulation tissues.

17 Claims, 1 Drawing Sheet

WOUND TREATMENT METHOD

BACKGROUND OF THE INVENTION

The present invention generally relates to wound care requiring dressings and more specifically is directed towards a sterile cellular synthetic wound dressing made of polyvinyl acetal.

Throughout history, many diverse materials of various origins have been used to treat skin wounds. By 1923, the British Pharmaceutical Codex, included 97 surgical material products which included products generally listed as medicated and unmedicated cotton wools, gauzes, tows, and lints; gauze and cotton tissues, bandages, jaconet, oiled silk and emplastrums. Emplastrums consist of a piece of white leather, hand spread with a plaster mass having a generally medicated composition. By 1949, the number of these products had decreased; however, the practitioner of 1923 would probably have been surprised to find that products had hardly changed from the products used some twenty five years earlier. Until 1960, advances in the design of wound management products had been spasmodic and limited to the adaption of available materials. Little or no attention was paid to the performance of the product and little consideration was given to different healing environments which were required by different wound types. From 1960 on, a new generation of products was developed based on the realization that the control of micro-environments was necessary if wound healing was to progress to the optimum degree.

Advances in the development of synthetic polymers produced the most radical changes in the wound care dressings as factors such as water vapor, oxygen permeability, bacterial impermeability, and selective absorption could be incorporated into new formulations along with specific requirements such as conformability, non-adherence, and adhesiveness. This family of polymeric products included polymeric foams, polymeric films, particulate and fibrous polymers, hydrogels and hydrocolloids.

The polymeric foams along with polymeric films were the first to be described as environmental dressings. LYOFOAM® and CORADERM® are polyurethane foams with a heat and pressure modified wound contact surface having a limited absorbent capacity while permeable to water vapor with low adherence to the wound site. LYOFOAM® is a closed cell foam and has been used in the management of pressure ulcers while CORADERM® is a thinner polyurethane "membrane" and has been found useful in initiating healing in long-term ischemic ulcers.

Certain wounds require debridement to facilitate new cell growth and to that end particulate and fibrous polymeric products are used. Such materials debride wounds by entrapment of wound exudate which contains proteins, enzymes and growth factors. These enzymes will break down the necrotic tissue and loosen the bonds between the necrotic tissue and the wound's healing surface. Such materials preferably create a moist environment that will encourage autolytic debridement and may take the form of a granule, paste, fibrous mat, acrylamide/agarose copolymer sheet or twisted staple hank.

Hydrogels are three dimensional cross-linked networks of hydrophilic polymers that are prepared from materials such as gelatin, polysaccharides, cross-linked polyacrylamide polymers, polyelectrolyte complexes, and polymers or copolymers derived from methacrylate esters. These interact with aqueous solutions by swelling to an equilibrium value and retaining a significant proportion of water within their structure. They are insoluble in water. By varying the nature of the polymer structure a range of water-binding behavior and thus mechanical surface and permeability properties can be obtained. The absorption, transmission, and performance result in the maintenance of a moist wound with a continuous moisture flux across the dressing and a sorption gradient that assists in the removal of toxic components from the wound area.

In contrast to the single polymer hydrogels described, the products designated as hydrocolloids are complex formulations that contain not only colloids but elastomeric and adhesive components. Hydrocollids have an adhesive formulation that gives an initial adhesion higher than some surgical adhesive tapes. After application, the absorption of transepidermal water vapor will modify the adhesive flow to maintain a high tack and adhesive performance throughout the period of use.

The optimum wound handling characteristics for products are expressed in general terms such as a) removal of excess exudate and toxic components; b) maintain a high humidity or moistness at the wound/dressing interface; c) allow gaseous exchange; d) provide thermal insulation; e) protect against secondary infection; f) free wound from particulate contaminants; and g) allow removal of dressing from patient without pain or trauma. Even with the advances in technology, it should be noted that there is no simple dressing that can produce the optimum micro environment for all wounds or for all the healing stages of a single wound.

Nurses classify the wound stage based on the following criteria.

- Stage I: Erythema not resolving within 30 minutes of pressure relief. Epidermis remains intact. Reversible with intervention.
- Stage II: Partial thickness loss of skin layers involving epidermis and possibly penetrating into but not through dermis. May present as blistering with erythema and/or induration; wound base moist and pink; painful, free of necrotic tissue.
- Stage III: Full-thickness tissue loss extending through dermis to involve subcutaneous tissue. Presents as shallow crater unless covered by eschar. May include necrotic tissue undermining sinus tract formation, exudate and/or infection. Wound base is usually not painful.
- Stage IV: Deep tissue destruction extending through subcutaneous tissue to fascia and may involve muscle layers, joint, and/or bone. Presents as a deep crater, unless covered by eshcar. May include necrotic tissue, undermining, sinus tract formation, exudate, and/or infection. Wound base is usually not painful. "Standards and Protocol for Pressure Ulcer Care", Norma J. Mash, p. 97, *Chronic Wound Care*, ©1990.

A clean moist wound surface enhances cellular migration. Maintenance of wound surface temperature facilitates cellular activity. Impediments to wound healing include necrotic tissue, infection and excess or pooled exudate. Necrotic tissue is an impediment to wound healing and can be removed through several techniques. There are a number of acceptable methods of debridement, including sharp debridement by cutting; mechanical debridement typically performed with a gauze, soft brush or sponge; gauze dressing debridement wet-to-dry and wet-to-wet; fluid bath or water propulsion; chemical or enzymatic debridement. Surgical debridement provides rapid and effective removal of necrotic tissue. Conventional debridement provides rapid and effective removal of necrotic tissue and can be used with other conventional topical surgery to enhance the clean-up of the wound. Enzymatic agents chemically break down necrotic tissue and transparent adhesive film dressings enhance leukocyte migration and resultant autolysis of necrotic tissue. *Chronic Wound Care* (supra.), pp. 101, 102.

Wound cleansing promotes removal of wound debris and bacteria from the wound surface; absorptive dressings are used to absorb excess exudate, obliterate dead space, and keep the wound surface moist. It should be noted that dead space impairs the wound healing process and predisposes the wound to abscess formation. Conversely, tight wound packing can impair circulation and damage healthy tissue.

In order to promote healing, it is necessary for the wound to be cleaned free of necrotic tissue. This tissue must be removed before healing takes place.

Non-adhesive polyurethane foam dressings such as ALLEVYN® and LYOFOAM® can be used on Stage II and Stage III wound types and provide some absorption while insulating the surface to prevent wound dehydration. It is specifically noted that these dressings should not be used with wound tunneling. *Chronic Wound Care*, ©1990, "Pressure Ulcer Management: A Nursing Challenge", Leslie A. Trudahl, p. 162.

Stage III and Stage IV ulcers heal by the process of granulation, wound contraction and epithelialization. Granulation involves the formation of collagen and new blood vessels. Regenerated collagen is not as elastic or strong as the dermis which has been destroyed. Wound contraction occurs when the wound edge pulls together at which time epithelization occurs.

Common factors that impair wound healing include the following:
Necrosis, slough and eschar
Prolonged inflammation
Hypoxemia
Vascular insufficiency
Protein malnutrition
Infection
Steriod medications
Dehydrated wound bed
Anemia
"How do you score? : Test your skills in Pressure Ulcer Management", p. 197, Joan E. Halpin-Landry, *Chronic Wound Care*, ©1990.

Debridement of necrotic tissue in the wound is important because necrotic tissue harbors bacteria and prevents healing. Necrotic tissue includes slough, a yellow, green, or grey necrotic debris that looks like string and has a consistency of glue or chewing gum; and eschar, a thick, black, leather-like crust of dead tissue often covering an underlying necrotic process. Selective debridement is preferable to non-selective debridement in that selective debridement only removes necrotic tissue while non-selective debridement removes healthy, healing and necrotic tissues. Non-selective debridement includes wet-to-dry gauze dressings, dry-to-dry gauze packings, wet-to-wet gauze dressings, forceful irrigation, hydrogen peroxide, Dakin's solution, radical sharp debridement using scissors or knife, and whirlpool. Non-selective debridement is usually chosen for excessive necrotic debris and eschar and for debris supporting an infective process in the wound. Non-selective debridement sacrifices viable tissue for rapid cleaning of the wound.

Presently selective debridement includes careful surgical debridement and certain topical proteolytic enzyme preparations such as streptodornase, papain, sutilains, streptokinase, collagenase, fibrinolysin, and deoxyribonuclease, which digest and dissolve necrotic slough and eschars.

A number of patents have been directed towards treatment of necrotic tissue in wounds. Hyrogel wound dressings for preventing pooling of wound exudate are shown in U.S. Pat. Nos. 4,909,244; 5,115,801; and 5,160,328. Hydrogel dressings are composed of cross linked polymers (polyethylene oxide or polyvinyl-pyrrolidone ). Water usually constitutes more than 90% of the dressing's composition and the same are used on Stage I, II, or III pressure ulcers and dermal ulcers. A proteolytic enzyme dressing performs by separation of non-viable, devitalized tissue, especially eschar tissue from viable tissue in a host organ. Topical dressings for burn protection used in absorbing necrotic tissues and exudate are shown by U.S. Pat. No. 3,648,692. This patent has a wound facing layer of dressing constructed of any of various neutral synthetic reticulated open-cell solid foam or sponge materials and covered with a barrier membrane, the thickness of the sponge facing layer being critical (preferably about one-sixteenth of an inch ) so that debris, fluids, etc. contained therein are accessible for phagocytic invasion from the body surface. If the layer is too thick, U.S. Pat. No. 3,64 8,692 teaches that segregated exudate located at the interface is not reached by the natural phagocytic action with the undesirable result that infection takes place and spreads within the dressing thereby delaying or preventing the healing process. Another foam sponge product of lyophilized hydrocolloid foam capable of absorbing body exudates is shown in U.S. Pat. No. 4,292,972. A cross-linked collagen sponge for wound dressings which absorbs exudates is shown by U.S. Pat. No. 4,759,354. The wound dressing is preferably constructed of a thin outer oxygen and vapor-permeable film; a layer of an absorbent adhesive such as hydrogel for adhering the wound dressing to the skin and for acting as a reservoir for wound exudate absorbed therein; and a layer of collagen, in the form of a sponge or film adapted for placement directly on the wound, the collagen layer being of smaller dimensions than the absorbent adhesive layer so that areas of the adhesive layer extending beyond the periphery of the collagen layer can be applied to the skin surrounding the wound to adhere the dressing in place.

A debriding tape which contains a proteolytic enzyme preferably subtilisin A or B used in debridement of eschar and necrotic tissue is shown in U.S. Pat. No. 4,668,22 8. In this debriding tape, a thin polyether polyurethane film coated with an acrylate type surgical pressure sensitive adhesive has a release paper sheet covering the adhesive coating. An opening is cut in the release paper and subtilisin A powder is applied to the cut out area which is in turn covered with a protective facing of release paper. As taught by this patent a highly evaporative dressing cannot be used in the debriding tape as it is necessary for water from (or placed on) the wound being treated, to be held in place under the dressing so that it puddles and serves to activate the enzyme and is not transmitted through the dressing, wicking the enzyme away from the necrotic tissue. The debriding tapes are to be used to debride grade two to grade four ischemic ulcers, or any wound containing necrotic tissue.

A burn healing study published in 1962 by Chardack et al. was initiated with the knowledge that pores of an open cell sponge of formalinized polyvinyl alcohol when embedded in living tissues are rapidly permeated by granulation tissue. The clinical experiences of Chardack et al. supported the previous conclusions that an open cell (formalinized)[1] polyvinyl alcohol sponge becomes and remains adherent to a denuded body surface, whether the latter has resulted from the excision of integument in clean planes or whether it has been filled in by granulation tissue. The adherence of the sponge is predicated upon proliferation of viable granulation tissue into the pores of the sponge. Adherence was confirmed at the first time check point 24 hours after placement. The material can be repeatedly washed, cleansed and ultimately be replaced by autografts. *Synthetic Substitutes For Skin*, Chardack et al. Plastic & Reconstructive Surgery, Vol. 30, No. 5 (Nov. 1962).

[1] added for edification

Autolysis is a method of selective debridement that has become accepted over the last several years as healthcare professionals have adopted theories of moist wound healing. Autolysis refers to self-digestion by the enzymes naturally present in wound fluids and the process of liquification of eschars. Autolysis could also be considered an organic technique because it enhances the body's own ability to rid itself of destroyed tissue. After debridement, wounds may become larger because all dead material has been removed which lays the ground work for healing to begin.

Four main types of synthetic dressings provide autolytic debriding action:
1). Moisture vapor permeable membrane
2). Polymeric membranes
3). Hydrogel dressings
4). Hydrocolloid semi-occlusive and occlusive dressings. "Using Synthetic Autolytic Debriding Agents for the Treatment of Full-Thickness Ulcers", Nora King, p. 97, *Chronic Wound Care*, ©1990.

SUMMARY OF THE INVENTION

The present invention involves the use in a Stage II, III or Stage IV wound of a cellular sponge dressing made of polyvinyl acetal having a pore size ranging from about 0.3–to about 1.mm, an absorptive capacity of up to 25 times its own weight in fluid, and a retained holding capacity of 16 times its own weight in fluid as per ASTM D-1117-80. The dressing when placed in an open wound (1) therapeutically manages Stage II, III & IV pressure and venous stasis ulcers; (2) immediately removes by wicking excess wound exudate from pressure and venous stasis ulcers leaving an optimal balance of fluid in contact with the wound surface and allowing the excess to be absorbed into the sponge itself; (3) selectively atraumatically debrides (SAD) necrotic tissue; and (4) mechanically removes partially autolyzed necrotic tissue atraumatically.

In the accompanying drawings, there is shown an illustrative embodiment of the invention from which these and other of objectives, novel features and advantages will be readily apparent.

DETAILED DESCRIPTION OF THE INVENTION

Figure 1:
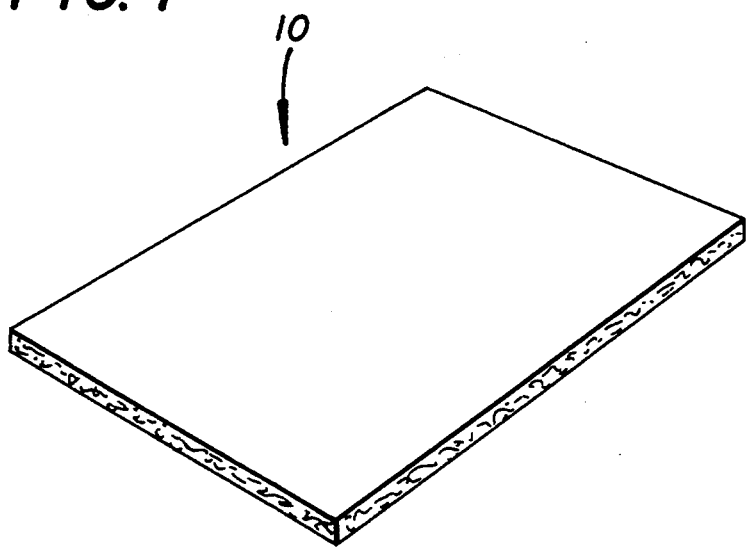
FIG. 1 shows a perspective view of a rectangular wound dressing of the invention.

The preferred embodiment and best mode of the invention is shown in FIG. 1. There are an estimated five million chronic wounds in the United States alone. Management of these wounds is often complicated by the presence of necrotic tissue, slough, and contaminants. With removal of these materials, optimum wound healing is allowed and reduction of the incident of infection is accomplished. Autolysis or breakdown of necrotic tissue via the body's own enzymes and repair mechanisms may be promoted by maintaining a moist wound healing environment. Furthermore, the very nature of autolysis produces fluids from the wound in addition to the normally occurring exudate. Excess fluids must be continuously removed from the wound to prevent pooling and subsequent breakdown of healthy wound tissue and surrounding skin. Autolysis via film dressings and gauze dressings are often used sequentially to debride necrotic wounds. Autolysis via film dressing is chosen initially to loosen necrotic tissue in shallow wounds and then gauze is used to provide mechanical debridement. The combination is felt to be less traumatic than management with gauze alone and faster than management via film .dressing autolysis alone. The film/gauze combination, however, introduces all the limitations and disadvantages of using films and gauze.

Figure 2:
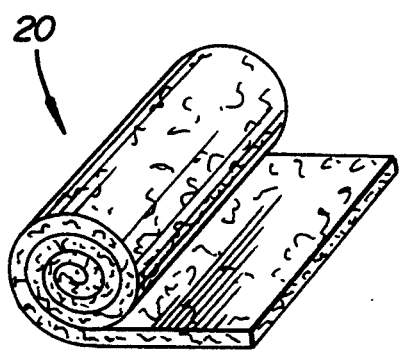
FIG. 2 shows a perspective view of a strip embodiment wound dressing of the invention.

There is, thus, a need for a treatment capable of debriding necrotic base wounds that is selective, atraumatic, fast, and is appropriate for Stage II, III and IV wounds of all depths and exudate levels, especially those wounds producing moderate to heavy exudate. The present dressing is made of a material described in U.S. Pat. No. 4,098,728 issued Jul. 4, 1978. The polyvinyl acetal sponge is made with a uniform pore size ranging from about 0.3 to about 1. mm diameter and is cut into a 10×10×0.6 cm thickness or 4"×4"×¼" wound dressing for insertion into Stage II, III and IV wounds. The sponge dressing 10 has a immediate wicking and the capacity to absorb water to the extent of 25 times the sponge weight and a retained holding capacity of 16 times its own weight in fluid as measured by ASTM D-1117-80. If desired, the length, width and thickness of the wound dressing can vary. The dressing is packaged sterile and cut to size. The dressing can also be pre-moistened with saline or water in a sterile peel pouch. An alternative embodiment is the strip dressing 20 shown in FIG. 2. The strip dressing 20 is preferably constructed of the same material cut into a strip like a roll of gauze having, a rectangular, square or circular cross section. The rectangular cross section is preferably on a 2 to 1 ratio, namely ½" to ¼" with the square cross section ¼ to "½ inch. Alternatively, the dressing can be folded rather than rolled and mechanically compressed to a 1 to 10 ratio in single or multiple directions for placement in the wound or under wound edges or within wound sinus tracts.

It was found that the aforenoted wound dressing was extraordinary in managing wounds with heavy exudate and could be packed or placed in a pressure position within the open wounds. The expected interaction of the dressing with various types of tissue in the wound would have been two fold, namely, (1) tissue attachment with the possibility of mechanical tissue debridement like gauze and the results of the Chardack research: non-selective and traumatic or (2) no mechanical interaction of the wound tissue with the dressing at the pore size used. However, the wound dressing 10 was surprisingly found to optimally absorb excess exudate, hence permitting necrotic tissue autolysis and selectively, atraumatically debrides (SAD) slough/adherent necrotic tissue from wounds including Stage IV pressure ulcers and venous stasis ulcers. Neither wound trauma nor disruption of granulation was observed. The necrotic tissue interaction of the inventive dressing with the wound, termed Selective, Atraumatic Debridement, has been clinically defined as a combination of quick and thorough autolysis with mechanical debridement occurring simultaneously through the selective and atraumatic adsorption of necrotic slough onto the dressing and out of the wound. The sponge wound dressing 10 also has the ability to absorb a high volume of wound exudate while allowing conformability to the wound topography and cushioning to the wound. The clinical observations with regard to pressure ulcers and venous stasis ulcers in the use of the inventive sponge dressings having a uniform pore size ranging from about 0.3 to about 1. mm diameter was that absorption capacity was increased compared to sponge dressings of smaller pore size ranges and was better than any available dressing presently being used. Conformability and the ability to maintain wound contact was present in the dressing along with accelerated liquification or autolytic debridement of necrotic tissue. Furthermore, the dressing had no attachment to healing and granulation tissue but did have attachment or adsorption of necrotic tissue bands to the sponge cellular material. Removal of the dressing from the wound resulted in selective debridement without trauma or damage to healthy tissue.

Comparisons of the present invention with known dressing materials is shown in Table I below.

TABLE I

|  |  |  |  |  |  |  |  |
|---|---|---|---|---|---|---|---|
| REMOVE EXCESS EXUDATE | ++ | + | + | ++ | + | + | − |
| MAINTAIN MOIST WOUND HEALING ENVIRONMENT | + | + | + | + | + | + | ++ |
| ALLOW GASEOUS EXCHANGE | ++ | ++ | + | − | + | − | − |
| THERMAL INSULATION | ++ | + | + | ++ | + | + | + |
| AFFORD PROTECTION AGAINST SECONDARY INFECTION (SOURCES EXTERNAL TO BODY) | + | + | + | ++ | ++ | ++ | ++ |
| FREE FROM PARTICULATE (FIBERS, LINT) | + | − − | − − | + | + | + | + |
| SIMPLE ATRAUMATIC REMOVAL (LOW ADHERENCE TO WOUND) | + | − | − | + | − | − | − |
| HIGH ABSORPTION CAPACITY PER DRESSING | ++ | − | + | ++ | − | − | − − |
| SLOW STRIKE THROUGH (WOUND EXUDATE ABSORBED THROUGH DRESSING) | ++ | − | − − | ++ | ++ | ++ | ++ |
| ACCEPTABLE HANDLING CHARACTERISTICS |  |  |  |  |  |  |  |
| TEAR RESISTANT (UPON REMOVAL) | ++ | − | − | + | ++ | + | ++ |
| DISINTEGRATION PROOF (WET AND DRY) | ++ | + | − | ++ | − | + | + |
| CONFORMABILITY TO WOUND | ++ | + | + | + | − | + | − |
| ABILITY TO PLACE UNDER WOUND EDGES | ++ | + | + | − | − | + | − |
| ABILITY TO PLACE IN WOUND TRACTS | ++ | + | + | − | − | + | − |
| STERILIZABLE | + | + | + | + | + | + | + |
| INSTANTANEOUS WICKING | ++ | ++ | ++ | − | − | − | − − |
| SUPPORTS AUTOLYSIS | ++ | − | + | − | − | − | + |
| SELECTIVE ATRAUMATIC DEBRIDEMENT | + | − | − | − | − | − | − |
| SOFT WOUND CONTACT SURFACE | + | − | − | + | + | + | + |
| COMPRESSIBLE | ++ | + | + | + | − | − | − |

Key:
+ = demonstrate this property
++ = strongly demonstrate this property
− = poor performance
− − = very poor performance Actual clinical studies were undertaken with the inventive dressing on 16 patients. A compilation of general patient data obtained from the studies is listed in Table II below.

TABLE II

| GENERAL PATIENT DATA | | | | | | | | | |
|---|---|---|---|---|---|---|---|---|---|
| PATIENT | | | TIME | | | WOUND | | | |
| # | Age | Sex | Entered | Completed | # Study Days | Type | Stage | Age (Mos.) | Prior Wound Treatments | SAD* |
| 1 | 78 | M | 11/10/92 | 11/11/92 | Hosp. | — | — | — | NS, BA, MD, T | NA |
| 2 | 78 | M | 12/02/92 | 02/12/93 | 72 | Press. U | IV | 6–12 | NS, BA, MD | YES |
| 3 | 79 | M | 11/10/92 | 12/18/92 | 32 | Press. U | III | 4–6 | NS, P, MD, T | NA |
|  |  |  | (Hosp. 12/18/92–01/09/93) |  |  |  |  |  |  |  |
| 3R | 79 | M | 01/09/93 | 02/07/93 | 29 | Press. U | III | 4–6 | NS, P, MD, T | YES |
| 4 | 94 | F | 11/10/92 | 11/15/92 | 6 | Press. U | IV | 1–3 | NS, BA, MD | NA |
| 5 | 94 | M | 10/26/92 | 11/21/92 | 25 | Press. U | III | <than 1 | NS, HG | NO |
| 6 | 80 | M | 10/26/92 | 11/21/92 | 25 | Press. U | IV | 4–6 | NS, BA | NA |
| 7 | 72 | F | 10/26/92 | 12/05/92 | 40 | Press. U | IV | 4–6 | NS, M, A, S | YES |
| 8 | — | M | 10/27/92 | 12/05/92 | 39 | Press. U | II | 1–3 | NS, HC | NA |
| 9 | 72 | F | 11/28/92 | 12/07/92 | 9 | Press. U | III | 4–6 | NS, BA, S | NA |
| 10 | 79 | F | 01/09/93 | 03/19/93 | 70 | Press. U | IV | 4–6 | NS, M, A, BA, S, MD | YES |
|  |  |  | (Hosp.) |  |  |  |  |  |  |  |
| 11 | — | F | 01/16/93 | 2/19/93 | 34 | Press. U | IV | <than 1 | NS, S, MD | YES |
| 12 | 79 | M | 02/07/93 | 04/12/93 | 64 | Press. U | IV | 4–6 | NS, S, MD | YES |

TABLE II-continued

| PATIENT | | | TIME | | | GENERAL PATIENT DATA | | | | |
|---|---|---|---|---|---|---|---|---|---|---|
| | | | | | | | WOUND | | | |
| # | Age | Sex | Entered | Completed | # Study Days | Type | Stage | Age (Mos.) | Prior Wound Treatments | SAD* |
| 13 | 83 | F | 01/19/93 | 03/06/93 | 46 | Press. U | IV | 4–6 | NS, BA, S, MD | YES |
| 14 | 70 | F | 01/20/93 | 03/20/93 | 59 | Rad. Reaction | IV | 6–12 | NS, BA, MD | NA |
| 15 | 83 | F | 01/30/93 | 04/12/93 | 72 | Press. U | IV | 4–6 | NS, BA, S, MD | YES |
| 16 | 75 | F | 03/04/93 | 05/06/93 | 63 | Press. U | IV | >than 12 | NS, BA, A, G | NA |

A — Calicium Alginate
BA — Bard Absorption Dressing
G — Gauze
HC — Hydrocolloids
HG — Hyrdogels
M — Mesalt
MD — Mechanical Debridement
NS — Normal Saline
P — Ferris Polymem Dressing
S — Surgical Debridement
T — Transparent Film
SAD — Selective Atraumatic Debridement
R — Wound Re-entered
NA — Not Applicable Reduction of the wound area was calculated on the basis of the area for an elipse and is shown in the following Table III. It should be noted that wound depth is not included even though measurements were taken as verification could not be established as to the accuracy of the measurements. Accurate wound depth measurements are difficult to uniformly obtain as the wound can have varying depths throughout its area and physical measurement of the depth of a wound is hard to gauge.

TABLE III

REDUCTION OF WOUND AREA

| Patient # | Initial Size (L × W) | % Area Reduction | | | | | | | | | |
|---|---|---|---|---|---|---|---|---|---|---|---|
| | | Week 1 | Week 2 | Week 3 | Week 4 | Week 5 | Week 6 | Week 7 | Week 8 | Week 9 | Week 10 |
| 1 | 1.5 × 2 | Hosp. | | | | | | | | | |
| 2 | 6 × 5.5 | — | — | — | — | 24 | 21 | 21 | 9 | 21 | 4 |
| 3 | 2 × 1.5 | — | 58 | 65 | 65 | 65 | Hosp. | | | | |
| 3R | 3.5 × 2.5 | 43 | 49 | 26 | 36 | End of study | | | | | |
| 4 | 2 × 1.5 | Patient expired on day 5 from cause determined to be unrelated to study. | | | | | | | | | |
| 5 | 8 × 5.5 | — | (9) | 25 | 25 | End of study | | | | | |
| 6 | 3.5 × 3 | — | (1) | (1) | (14) | Hosp. | | | | | |
| 7 | 5 × 4.3 | — | (5) | (19) | (19) | 22 | 26 | Hosp. | | | |
| 8 | 1.3 × 3 | — | 62 | 89 | 77 | 85 | End of study | | | | |
| 9 | 10 × 10 | 0 | Hosp. | | | | | | | | |
| 10 | 4.5 × 4 | 33 | 12 | 50 | 58 | 58 | 78 | 78 | 78 | 72 | End of Study |
| 11 | 4 × 3.5 | 25 | — | 71 | 71 | Hosp. | | | | | |
| 12 | 4.5 × 2 | 11 | (4) | 22 | 0 | 20 | 11 | 30 | 18 | 5 | End of study |
| 13 | 7 × 3.5 | (14) | (14) | (29) | (31) | (43) | (34) | (23) | End of study | | |
| 14 | | Radiation wound — dimensions unchanged for duration of study period | | | | | | | | | |
| 15 | 6 × 4.7 | 19 | 21 | 7 | 29 | 37 | 47 | 44 | 50 | 45 | 51 |
| 16 | 4.8 × 4 | 18 | (5) | (4) | 22 | — | 22 | 22 | 22 | 22 | End of study |

Wound areas were calculated by the area for an ellipse.
— No data avaiable; wound not evaluated.
( ) Represent negative percentage values.

The following narrative case studies taken from tables II and III above show unique healing effects of the inventive dressing on wounds of various patients particularly in regard to the SAD of Stage IV wounds.

EXAMPLE 1 PATIENT #2

The patient was a 78 year old male, 5'5", 125 lbs., bedbound and immobile in fair condition with tender/poor skin condition. The patient was housed in a nursing home. The study commenced on Nov. 10, 1992, was halted due to hospitalization of patient on Nov. 11, 1992. The study was restarted on Dec. 2, 1992 on a Stage IV pressure ulcer located on the right elbow of the patient measuring 6.0 cm length×5.5 cm width×0.5 cm deep. The wound had been in existence over 6 months and had the appearance of healthy pink granulation tissue with yellow wet necrotic tissue and slough, had serous drainage and was classified as a non-responsive wound. The skin around the wound was macerated. Previous treatments were numerous and included the absorption agent Bard Absorption Dressing. There was mechanical debridement with wet-to-dry dressings using a normal saline solution. The cleaning agent was normal saline. The patient response to this previous treatment was a deterioration of the wound. At the time of application of the inventive dressing, the wound base was a combination of healthy pink granulation tissue and yellow wet necrotic tissue. Undermining tunnels were present. On Feb. 5, 1993, the wound was nearly 100% granulated and measured 5.8 cm in length×4.5 cm in width with unmeasurable depth. The granulation tissue was healthier than the prior weeks and scattered yellow eschar was present. The wound still had serous exudate but had slight peripheral wound maceration. Dressing changes were undertaken at the rate of 14 per week. The inventive dressing removed the necrotic tissue while managing this heavily exudating wound. Selective atraumatic debridement was observed in the patient.

EXAMPLE 2 PATIENT #7

The patient was a female age 72 bedbound and immobile with tender/poor skin condition having a Stage IV pressure ulcer wound in the left hip. The wound was in poor condition with combined yellow wet necrotic tissue and healthy pink granulation tissue. The patient was housed in a nursing home. The wound had a combination of granulation tissue and necrotic tissue base and undermining tunnels. The skin was healthy around the wound. Autolysis occurred with establishment of 100% granulation tissue base in approximately 5 weeks, namely from the treatment start of Oct. 26, 1992 to Dec. 5, 1992. On Dec. 7, 1992, the patient was hospitalized. Wound dimensions were reduced from 5.0 cm in length×4.3 cm in width×2 cm deep at the time of application of the inventive dressing to 4 cm in length×4 cm in width×2 cm in depth. The skin was still healthy around the wound. Dressing changes were undertaken at the rate between 7 and 14 per week. Several times the inventive dressings were left on for a period of 24 hours. Selective atraumatic debridement was observed in the patient.

EXAMPLE 3 PATIENT #10

The patient was a 79 year old female with a height of 5'5"and weight of 135 lbs. with a tender/poor skin condition confined to a chair or wheelchair with full mobility. The patient was housed in a nursing home. The wound was a Stage IV sacral pressure ulcer and had 80% granulation tissue base with 20% necrotic slough and had not responded to previous treatment including the use of absorption agents; namely, sodium chloride impregnated dressing, calcium alginates, and Bard Absorption Dressing. Surgical debridement and mechanical debridement using wet-to-dry dressings with normal saline had also been used. The cleaning agent was normal saline. The duration of the wound was from 4–6 months prior to application of the invention and the wound was non-responsive and had deteriorated from previous treatment. The patient entered into treatment on Jan. 9, 1993 with the pressure ulcer wound 4.0 cm in length×4.5 cm in width×2.0 cm. On Feb. 19, 1993, the wound was 100% granulation tissue and reduced in size to 2.0 cm in length×. 2.0 cm in width×. 2.3 cm deep and selective atraumatic debridement was attributed to inventive dressing treatment. Dressing changes were undertaken at the rate of 14 per week. Several times the inventive dressings were left on a period of 24 hours. Selective atraumatic debridement was observed in the patient.

EXAMPLE 4 PATIENT #11

A female patient entered into study on Jan. 16, 1993 with an irregularly shaped Stage IV pressure ulcer on right buttock measuring 4.0 cm in length×3.5 cm in width×3.0 cm deep. The overall skin condition was healthy and normal. The patient was bedfast with limited mobility and was housed in a nursing home. The duration of the wound was less than one month and the wound base on Jan. 9, 1993 was approximately 100% mixed yellow necrotic tissue with eschar. Previous treatment included debridement with surgical instruments and mechanical debridement with a wet-to-dry dressing using hypergel solution. The cleaning agent used was normal saline. The wound response to this treatment resulted in deterioration. On Feb. 12, 1993, approximately one month after treatment the entire wound surface was measured 2.0 cm in length×2.0 cm in width×1.75 cm deep. The base was 90% healthy pink granulation tissue and 10% yellow necrotic tissue. The patient's condition required hospitalization on Feb. 19, 1993; the patient's wound was discontinued from this study. Selective atraumatic debridement of the wound was observed and felt to be due to the inventive dressing treatment. Dressing changes were undertaken at a rate of 14 per week.

EXAMPLE 5 PATIENT #11

A female patient, age 83, height 5'7" and weight of 109 lbs. with overall skin condition tender and poor, entered into study on Jan. 30, 1993 with 100% pink granulation tissue. The skin around the wound was healthy. The patient was bedfast with very limited mobility and was housed in a nursing home. Her Stage IV sacral pressure ulcer wound had a prior duration of 4–6 months and measured 6.0 cm in length×4.7 cm in width×2.2 cm deep with a condition of "red" granulating. The wound was previously treated with an absorption agent namely Bard Absorption Dressing and mechanical debridement using wet-to-dry dressings using normal saline solution, surgical debridement was performed 3 months prior to study. The wound was cleaned with normal saline. Moderate improvement was shown in response to the previous treatment. The patient was then treated with the subject wound dressing. Three weeks later, the wound was 80% granulation tissue with 20% yellow necrosis which 1 week later resumed 100% healthy pink granulation tissue status. The patient "roller coastered" for several weeks as the general medical condition changed. On Apr. 14, 1993, when discontinued from study, the patient's wound was 4.6 cm in length×3.0 cm in width×0.7 cm deep. Dressing changes were undertaken at the rate of 14 per week. Selective atraumatic debridement was observed in the patient.

The same female patient also had a Stage IV hip pressure ulcer measuring 7.0 cm in length×3.5 cm in width×0.7 cm deep on Jan. 19, 1993. There was no change in response to previous treatment. Her wound was partially necrotic on initial evaluation. There was no improvement in this wound.

Three of the patients numbers 1,4 and 9 did not have a long enough study time to effectively evaluate the therapeutic effect of the dressing (Note: Patient #1 had multiple wounds; the patient was reentered as Patient #2 with a different wound under study). However eleven (11) out of the remaining thirteen (13) received a therapeutic effect. These eleven (11) patients showed a 45% reduction in wound area at week 5. It should be noted that the patients had been treated with other wound treatments to no effect and that the age of the wounds with the exception of Patients #5 and #11 was quite old. Patients #6 and #13 showed an adverse effect. Selective atraumatic debridement was observed in 8 of the 9 patients with necrotic tissue present in the wound. The ninth patient (Patient #5) had a new wound with 100% necrotic tissue and was recommended for surgical debridement.

It should be noted that in certain patients the inventive wound dressing was left on the patient for a number of days without changing the dressing, with the wound dressing being easily removed from the patient. (Patient

3-6 days; Patient #5-2 days; Patient #6-2 days; Patient #8-2 days.)

Thus, the wound dressing 10 goes into wound cavities and performs selective atraumatic debridement by wicking the necrotic tissue and slough from the wound while conforming to the wound and maintaining its shape in the wound, keeping the wound surface moist and promoting healing. The dressing is held in place by an appropriate secondary dressing such as tape, film or the like. The simple application allows folding or layering for deep cavity wounds with placement under detached wound margins. Because of the physical nature of the sponge dressing it can be trimmed or cut for the particular wound without producing lint, fibers or other debris. The high moisture vapor transmission rate helps prevent skin maceration while maintaining the body temperature at the wound site. The sponge structure also allows exchange of gases including moisture vapor and oxygen through the porous structure of the dressing. Necrotic tissue and slough are incorporated into the sponge body by absorption so that the wound is cleaned when the sponge is removed atraumatically. Significant quantities of fluid exudates are absorbed into the dressing and removed from the wound surface. The sponge dressing changes ranged from twice a day to a six day period, commonly at each 12 hour period. The simple one piece atraumatic removal is enabled by the high wet strength of the material to prevent tearing upon removal and removal does not leave any dressing residue which must be flushed from the wound prior to redressing. The wound dressing maintained a moist wound surface while allowing natural autolysis and liquification of necrotic tissues by the enzymes of the body. The wound dressing was also observed to encourage epithelialization. Since the very nature of autolysis produces fluids from the wound in addition to normally occurring exudate, excess fluids must be removed from the wound to prevent fluid pooling breakdown of healthy wound tissue and surrounding skin. The ease of removal of the inventive dressing and the selective atraumatic debridement of the slough and necrotic tissue without damage to the granulation tissues was an unexpected result. Adherence to viable tissue would cause damage to healing tissue through injury to small blood vessels and regenerating cells.

Experienced clinicians have noted the following unexpected results in using the inventive dressing to treat wounds: (1) wounds were clean and bacterial infection reduced or eliminated; (2) drainage of wound secretion was diminished; (3) formation of new granulation tissue was improved and granulation tissue was not damaged by dressing removal; (4) undermined edges of the pressure sores were closed; (5) formation of the epithelium was stimulated; (6) dressing would be used with wounds having undermining tunnels; (7) the general condition of the wound improved up to five weeks and then generally maintained the area; and (8) slough and necrotic tissue are removed without damage to granulation tissue and without pain to the patient.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A method of treatment of Stage II, III and IV wounds in a mammal comprising the steps and IV wounds in a mammal comprising the steps of:
    a) inserting a sterile surgical dressing constructed of a sterile one piece substantially uniform polyvinyl acetal material into an open wound;
    b) conforming the dressing having an average pore diameter of at least 0.3 mm, to the open wound so that it conforms to the general configuration of the open wound and immediately begins to absorb wound exudate from the wound;
    c) allowing the surgical dressing to remain in the wound to autolyze slough and necrotic tissue from the wound and absorb excess wound exudate from the wound; and
    d) removing the surgical dressing to debride the necrotic tissue of the wound without appreciably damaging granulation tissues.

2. A method of treating a wound as claimed in claim 1 wherein said wound is a pressure ulcer.

3. A method of treating a wound as claimed in claim 1 wherein said wound is a venous stasis ulcer.

4. A method of treating a wound as claimed in claim 1 wherein said sterile surgical dressing is allowed to remain in said open wound a period not greater than 12 hours.

5. A method of treating a wound as claimed in claim 1 wherein said sterile surgical dressing is in a strip form.

6. A method of treatment of Stage IV wounds comprising the steps of:
    a) inserting a sterile surgical dressing constructed of a polyvinyl acetal having a pore size diameter ranging from about 0.3 to about 1. mm which is able to immediately wick fluids into an open wound;
    b) allowing the wound to autolyze so that necrotic tissue is absorbed into the surgical dressing and wound exudate is wicked into the sterile surgical dressing; and
    c) removing the sterile surgical dressing from the wound to selectively atraumatically debride the wound.

7. A method of treating a wound as claimed in claim 6 wherein said sterile surgical dressing is left in the open wound not more than 12 hours.

8. A method of treating a wound as claimed in claim 6 wherein said sterile surgical dressing is in a strip form.

9. A method of treating a wound as claimed in claim 6 wherein said sterile surgical dressing is in a strip form.

10. A method of treating a wound as claimed in claim 6 wherein said sterile surgical dressing has a rectangular configuration 10 cm width×10 cm length×0.6 cm thickness.

11. A method of treating Stage II, III and IV wounds which produce moderate to heavy exudate comprising the steps of:
    a) inserting a surgical dressing constructed of a polyvinyl acetal having a pore diameter greater than 0.3 mm and a capacity to absorb up to 25 times its own weight in fluid into an open wound so that it conforms to the general configuration of the open wound and immediately begins to absorb wound exudate;
    b) leaving the surgical dressing in the wound a sufficient period to autolyze necrotic tissue from the wound and absorb the same in the pores of the dressing while immediately absorbing wound exudate produced by the wound and wound exudate produced by autolysis; and c) removing the sterile surgical dressing to atraumatically debride the wound without disrupting granulation tissue of the wound.

12. A method of treating a wound as claimed in claim 11 wherein said period the dressing is left in the wound ranges from 8–12 hours.

13. A method of autolytically debriding Stage IV pressure ulcer wounds producing moderate to heavy exudate to remove necrotic tissue, slough and wound exudate without trauma comprising the steps of:
   a) inserting a sterile surgical dressing constructed of a polyvinyl acetal having a pore diameter ranging from 0.3 to about 1. mm and a capacity to absorb and retain at least 16 times its own weight in water into an open wound so that it conforms to the general configuration of the open wound;
   b) leaving the sterile surgical dressing in the wound a period of at least 12 to 24 hours to promote autolysis using the body's own repair enzymes to break down necrotic tissue,
   c) simultaneously removing exudate and necrotic tissue from the wound and absorbing a majority of the volume of the wound exudate from the wound; and
   e) removing the sterile surgical dressing to debride the wound without disrupting granulation tissue of the wound.

14. The method of claim 13 wherein said sterile surgical dressing in paragraph a) is wetted with saline.

15. The method of claim 13 wherein said sterile surgical dressing in paragraph a) is dry.

16. A method of autolytically debriding Stage IV pressure ulcer wounds producing moderate to heavy exudate to remove necrotic tissue, slough and wound exudate without trauma comprising the steps of:
   a) inserting a sterile surgical dressing constructed of a polyvinyl acetal having a pore diameter ranging from about 0.3 to about 1. mm and a capacity to absorb up to 25 times its own weight in water into an open wound so that it conforms to the general configuration of the open wound;
   b) leaving the sterile surgical dressing in the wound a period in excess of 24 hours to promote selective atraumatic debridement using the body's own repair enzymes to break down necrotic tissue;
   c) simultaneously removing exudate by absorbing a majority of the volume of the wound exudate while mechanically removing autolyzed necrotic tissue from the wound; and
   d) removing the sterile surgical dressing to debride the wound without disrupting granulation tissue of the wound.

17. A method of treating Stage II, III and IV pressure and venous stasis ulcer wounds which produce moderate to heavy exudate comprising the steps of:
   a) inserting a surgical dressing constructed of a polyvinyl acetal having a uniform pore density and a capacity to absorb multiples of its own weight in water into and open wound so that it conforms to the general configuration of the open wound;
   b) immediately removing by wicking excess wound exudate from pressure and venous stasis ulcers leaving an optimal balance of fluid in contact with the wound surface and allowing the excess to be absorbed into the sponge itself;
   c) leaving the surgical dressing in the wound a sufficient period to selectively atraumatically debride necrotic tissue from the wound and absorb the same in the pores of the dressing while immediately absorbing wound exudate produced by the wound exudate produced by autolysis; and
   d) removing the sterile surgical dressing to debride the wound without disrupting granulation tissue of the wound.

* * * * *